United States Patent
Birk (10) Patent No.: US 9,326,877 B2
(45) Date of Patent: May 3, 2016

(54) APPARATUS AND METHOD FOR INTRAGASTRIC BALLOON WITH IN SITU ADJUSTMENT MEANS

(75) Inventor: Janel Birk, Oxnard, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 484 days.

(21) Appl. No.: 11/540,177

(22) Filed: Sep. 29, 2006

(65) Prior Publication Data
US 2008/0172079 A1    Jul. 17, 2008

(51) Int. Cl.
A61M 29/00    (2006.01)
A61F 5/00    (2006.01)

(52) U.S. Cl.
CPC ............... *A61F 5/003* (2013.01); *A61F 5/0036* (2013.01)

(58) Field of Classification Search
CPC ............... A61F 5/0003; A61F 5/0013; A61F 5/003–5/046; A61B 17/12113; A61B 17/1236; A61B 2017/12054; A61B 2017/12081
USPC .................. 600/31; 606/153, 192; 623/23.67, 623/23.65, 27.64; 137/843–847, 850
See application file for complete search history.

(56) References Cited

U.S. PATENT DOCUMENTS

| | | | |
|---|---|---|---|
| 1,702,974 A | 2/1929 | MacDonald | |
| 2,163,048 A | 6/1939 | McKee | |
| 2,183,900 A * | 12/1939 | Voit et al. | 137/223 |
| 2,387,433 A * | 10/1945 | Fenton | 473/611 |
| 3,667,081 A | 6/1972 | Burger | |
| 3,719,973 A | 3/1973 | Bell | |
| 3,840,018 A | 10/1974 | Heifetz | |
| 3,919,724 A | 11/1975 | Sanders et al. | |
| 4,118,805 A | 10/1978 | Reimels | |
| 4,430,392 A | 2/1984 | Kelley et al. | |
| 4,485,805 A | 12/1984 | Foster, Jr. | |
| 4,545,367 A * | 10/1985 | Tucci | 128/898 |
| 4,592,355 A | 6/1986 | Antebi | |

(Continued)

FOREIGN PATENT DOCUMENTS

| CN | 1250382 | 4/2000 |
|---|---|---|
| CN | 1367670 | 9/2002 |

(Continued)

OTHER PUBLICATIONS

Patient Information Brochure, "Living With the Bib/BioEnterics Intragastric Balloon Program," Inamed Health, May 1, 2005, 1-10 pp.

(Continued)

*Primary Examiner* — Katherine Rodjom
*Assistant Examiner* — Jonathan Hollm
(74) *Attorney, Agent, or Firm* — Gordon & Jacobson, P.C.

(57) ABSTRACT

An intragastric balloon and method of adding and/or removing fluid therefrom are disclosed. The intragastric balloon includes a shell, a grasping tab, and a self-sealing portion. A gastroscopic instrument which includes a grasping tool is inserted into the stomach of a patient and used to grasp the grasping tab located on the surface of the shell. Using the grasping tool, the intragastric balloon is securely fastened to the gastroscopic instrument. A filling instrument, such as a needle, is advanced through the self-sealing portion of the shell for the filling or deflating of the intragastric balloon. After inflation or deflation is complete, the filling instrument is then withdrawn from the balloon and the gastroscopic instrument withdrawn from the stomach.

23 Claims, 8 Drawing Sheets

(56) References Cited

U.S. PATENT DOCUMENTS

| | | |
|---|---|---|
| 4,598,699 A | 7/1986 | Garren et al. |
| 4,607,618 A | 8/1986 | Angelchik |
| 4,636,213 A | 1/1987 | Pakiam |
| 4,694,827 A | 9/1987 | Weiner et al. |
| 4,723,547 A | 2/1988 | Kullas et al. |
| 4,739,758 A | 4/1988 | Lai |
| 4,881,939 A | 11/1989 | Newman |
| 4,930,535 A | 6/1990 | Rinehold |
| 4,969,899 A | 11/1990 | Cox, Jr. |
| 5,074,868 A | 12/1991 | Kuzmak |
| 5,084,061 A | 1/1992 | Gau et al. |
| 5,211,371 A | 5/1993 | Coffee |
| 5,226,429 A | 7/1993 | Kuzmak |
| 5,289,817 A | 3/1994 | Williams et al. |
| 5,449,368 A | 9/1995 | Kuzmak |
| 5,527,340 A | 6/1996 | Vogel |
| 5,601,604 A | 2/1997 | Vincent |
| 5,658,298 A | 8/1997 | Vincent et al. |
| 5,693,014 A | 12/1997 | Abele et al. |
| 5,725,507 A | 3/1998 | Petrick |
| 5,748,200 A | 5/1998 | Funahashi |
| 5,819,749 A | 10/1998 | Lee et al. |
| RE36,176 E | 3/1999 | Kuzmak |
| 5,915,407 A * | 6/1999 | West ............................ 137/223 |
| 5,938,669 A | 8/1999 | Klaiber et al. |
| 6,074,341 A | 6/2000 | Anderson et al. |
| 6,102,678 A | 8/2000 | Peclat |
| 6,102,897 A | 8/2000 | Lang |
| 6,102,922 A | 8/2000 | Jakobsson et al. |
| 6,152,922 A | 11/2000 | Ouchi |
| 6,290,575 B1 | 9/2001 | Shipp |
| 6,454,699 B1 | 9/2002 | Forsell |
| 6,454,785 B2 | 9/2002 | De Hoyos Garza |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,547,801 B1 | 4/2003 | Dargent et al. |
| 6,579,301 B1 | 6/2003 | Bales et al. |
| 6,629,776 B2 | 10/2003 | Bell et al. |
| 6,733,512 B2 | 5/2004 | McGhan |
| 6,733,513 B2 | 5/2004 | Boyle et al. |
| 6,746,460 B2 | 6/2004 | Gannoe et al. |
| 6,840,257 B2 | 1/2005 | Dario et al. |
| 6,994,095 B2 * | 2/2006 | Burnett ........................ 128/898 |
| 7,020,531 B1 | 3/2006 | Colliou et al. |
| 7,037,344 B2 | 5/2006 | Kagan et al. |
| 7,056,305 B2 * | 6/2006 | Garza Alvarez ............. 604/191 |
| 7,214,233 B2 | 5/2007 | Gannoe et al. |
| 7,223,277 B2 | 5/2007 | DeLegge |
| 7,883,525 B2 | 2/2011 | DeLegge |
| 8,075,582 B2 | 12/2011 | Lointier |
| 8,162,969 B2 | 4/2012 | Brister |
| 8,187,297 B2 | 5/2012 | Makower |
| 2002/0095181 A1 | 7/2002 | Beyar |
| 2002/0139208 A1 | 10/2002 | Yatskov |
| 2002/0173698 A1* | 11/2002 | Morningstar .................. 600/29 |
| 2002/0183782 A1* | 12/2002 | Tsugita et al. ................ 606/200 |
| 2003/0073880 A1 | 4/2003 | Polsky et al. |
| 2003/0106761 A1 | 6/2003 | Taylor |
| 2003/0187474 A1* | 10/2003 | Keegan et al. ................ 606/200 |
| 2005/0033332 A1 | 2/2005 | Burnett |
| 2005/0055039 A1 | 3/2005 | Burnett et al. |
| 2005/0131485 A1* | 6/2005 | Knudson et al. ................ 607/40 |
| 2005/0190070 A1 | 9/2005 | Rudduck et al. |
| 2005/0192615 A1 | 9/2005 | Torre et al. |
| 2005/0240279 A1 | 10/2005 | Kagan et al. |
| 2005/0250979 A1 | 11/2005 | Coe |
| 2005/0261711 A1 | 11/2005 | Okada et al. |
| 2005/0267595 A1 | 12/2005 | Chen et al. |
| 2005/0267596 A1 | 12/2005 | Chen et al. |
| 2005/0273060 A1 | 12/2005 | Levy |
| 2006/0020278 A1* | 1/2006 | Burnett et al. ................ 606/153 |
| 2006/0025799 A1 | 2/2006 | Basu |
| 2006/0069403 A1 | 3/2006 | Shalon et al. |
| 2006/0142700 A1 | 6/2006 | Sobelman et al. |
| 2006/0229702 A1* | 10/2006 | Agnew .......................... 623/1.11 |
| 2007/0016262 A1 | 1/2007 | Gross et al. |
| 2007/0083224 A1 | 4/2007 | Hively |
| 2007/0118168 A1 | 5/2007 | Lointier |
| 2007/0135829 A1* | 6/2007 | Paganon ....................... 606/192 |
| 2007/0147170 A1 | 6/2007 | Hood et al. |
| 2007/0149994 A1 | 6/2007 | Sosnowski |
| 2007/0156248 A1 | 7/2007 | Marco et al. |
| 2007/0173881 A1* | 7/2007 | Birk et al. ..................... 606/192 |
| 2007/0288033 A1 | 12/2007 | Murature et al. |
| 2008/0071305 A1 | 3/2008 | DeLegge |
| 2008/0172079 A1 | 7/2008 | Birk |
| 2008/0208240 A1 | 8/2008 | Paz |
| 2008/0243071 A1* | 10/2008 | Quijano et al. ........... 604/103.02 |
| 2008/0255601 A1 | 10/2008 | Birk |
| 2009/0082644 A1 | 3/2009 | Li |
| 2009/0131968 A1 | 5/2009 | Birk |
| 2009/0259246 A1 | 10/2009 | Eskaros et al. |
| 2010/0087843 A1 | 4/2010 | Bertolote et al. |
| 2010/0100079 A1 | 4/2010 | Berkcan et al. |
| 2010/0168783 A1 | 7/2010 | Murature et al. |
| 2010/0174307 A1 | 7/2010 | Birk |
| 2010/0274194 A1 | 10/2010 | Sobelman et al. |

FOREIGN PATENT DOCUMENTS

| | | |
|---|---|---|
| DE | 88 04 765 U1 | 5/1989 |
| DE | 88 04 765 U1 | 5/1998 |
| DE | 102007025312 | 11/2008 |
| EP | 1396242 | 3/2004 |
| EP | 1396243 | 3/2004 |
| EP | 1774929 | 4/2007 |
| EP | 2095798 | 9/2009 |
| FR | 2797181 | 2/2001 |
| FR | 2823663 | 10/2002 |
| FR | 2852821 A1 * | 10/2004 |
| FR | 2855744 | 12/2004 |
| FR | 2941617 | 8/2010 |
| GB | 2086792 | 5/1982 |
| JP | 63-279854 | 11/1988 |
| JP | 1049572 | 2/1989 |
| JP | 63-264078 | 10/1998 |
| WO | WO 00/15158 | 3/2000 |
| WO | WO 01/10359 | 2/2001 |
| WO | WO 01/49245 | 7/2001 |
| WO | WO 01/66166 | 9/2001 |
| WO | WO 02/35980 | 5/2002 |
| WO | WO 03/055419 | 7/2003 |
| WO | WO 03/105732 | 12/2003 |
| WO | WO 2004/019671 | 3/2004 |
| WO | WO2005/007231 | 1/2005 |
| WO | WO 2006/020370 | 6/2006 |
| WO | WO 2006/063593 | 6/2006 |
| WO | WO 2006/090018 | 8/2006 |
| WO | WO 2006/118744 | 11/2006 |
| WO | WO 2007/011086 | 10/2007 |
| WO | WO 2010/042062 | 4/2010 |

OTHER PUBLICATIONS

Bib Data Sheet Directions for Use, "BioEnterics Intragastric Balloon System," Inamed Health, 1-12 pp.

BIB Bioenterics Intragastric Balloon Program, "Taking the Next Step/Take Control of Your Weight and Your Life," Inamed Health, Apr. 29, 2004, 1-9 pp.

BIB Bioenterics Intragastric Balloon Program, "Take Control of Your Weight and Your Life/The Solution for You," Inamed Health, Jan. 19, 2004, 1-2 pp.

Baggio et al. "Biology of Integrins: GLP-1 and GIP"; Gastroenrology; V. 132; pp. 2131-2157; 2007.

Berne et al.; "Physiology"; V. 5; pp. 55-57, 210, 428 540, 579, 584, 591; 2004.

Boulant et al.; "Cholecystokinin in Transient Lower Oesophageal Sphincter Relation Due to Gastric Distension in Humans"; Gut; V. 40; pp. 575-581; 1997.

(56) References Cited

OTHER PUBLICATIONS

Bradjewin et al.; "Dose Ranging Study of the Effects of Cholecystokinin in Healthy Volunteers"; J. Psychiatr. Neurosci.; V. 16 (2); pp. 91-95; 1991.

Chaudri, Owais; "Can Gut Hormones Control Appetite and Prevent Obesity?" Diabetes Care, V. 31, Supp. 2, Feb. 2008.

Cohen et al.; "Oxyntomodulin Suppresses Appetite and Reduces Food in Humans"; J. Clin. Endocrinol. Metab.; V. 88; pp. 4696-4701; 2003.

Dakin et al.; "Oxyntomodulin Inhibits Food Intake in the Rat"; Endocrinology; V. 142; pp. 4244-4250; 2001.

Dakin et al.; "Peripheral Oxyntomodulin Reduces Food Intake and Body Weight gain in Rats" Endocrinology; V. 145; pp. 2687-2695; 2004.

Davison, J.; "Activation of Vagal-Gastric Mechanoreceptors by Cholecystokinin"; Proc. West. Pharmocol. Soc.; V. 29; pp. 363-366; 1986.

Ekblad et al.; "Distribution of Pancreatic Peptide and Peptide-YY"; Peptides; V. 23; pp. 251-261; 2002.

Greenough et al.; "Untangling the Effects of Hunger, Anxiety and Nausea on Energy Intake During Intravenous Cholecystokinin Octapeptide (CCK-8) Infusion" Physiology and Behavior; V. 65 (2); pp. 303-310, 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; "Gastrointestinal Factors in Hunger and Satiety"; Neurosci. and Behav. Rev.; V. 6; pp. 145-164; 1982.

Kissileff et al.; "Peptides that Regulate Food Intake: Cholecystokinin and Stomach Distension Combine to Reduce Food Intake in Humans"; Am. J. Physiol. Regul. Integr. Comp. Physiol.; V. 285; pp. 992-998; 2003.

Naslund et al.; "Prandial Subcutaneous Injection of Glucagon-Like Peptide"; Br. J. Nutr.; V. 91; pp. 439-446; 2004.

Renshaw et al. "Peptide YY: A Potential Therapy for Obesity"; Current Drug Targets; V. 6; pp. 171-179; 2005.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; 2001.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

S.A. Xanthakos, "Bariatric surgery for extreme adolescent obesity: Indications, outcomes, and physiologic effects on the gut-brain axis", Elsevier Pathophysiology 15, 2008, pp. 135-146.

* cited by examiner

APPARATUS AND METHOD FOR INTRAGASTRIC BALLOON WITH IN SITU ADJUSTMENT MEANS

BACKGROUND OF INVENTION

1. Field of the Invention

The present invention is directed to devices and methods that enable inflatable intragastric balloons used for the treatment of obesity to be filled, and in particular to devices and methods that enable the intragastric balloon to be filled, adjusted, or deflated while the device itself is in the stomach.

2. Description of the Related Art

Intragastric balloons are well known in the art as a means for weight loss and treating obesity. One such inflatable intragastric balloon is described in U.S. Pat. No. 5,084,061 and is commercially available as the BioEnterics Intragastric Balloon System (sold under the trademark BIB®). These devices are designed to provide therapy for moderately obese individuals who need to shed pounds in preparation for surgery, or as part of a dietary or behavioral modification program.

The BIB® System, for example, consists of a silicone elastomer intragastric balloon that is inserted into the stomach and filled with fluid. Commercially available gastric balloons are filled with saline solution or air. The intragastric balloon functions by filling the stomach and enhancing appetite control. Placement of the intragastric balloon is nonsurgical, usually requiring no more than 20-30 minutes. The procedure is performed gastroscopically in an outpatient setting, typically using local anesthesia and sedation. Placement is temporary, and intragastric balloons are typically removed after six months.

Most intragastric balloons utilized for this purpose are placed in the stomach in an empty or deflated state and thereafter filled (fully or partially) with a suitable fluid through a filler tube. The filler tube can be either removable or permanently attached to the balloon. The removable filler tube is typically attached prior to initial placement of the gastric balloon and then removed after inflation. The balloon occupies space in the stomach, thereby leaving less room available for food and creating a feeling of satiety for the overweight patient. Clinical results with these devices show that for many overweight patients, the intragastric balloons significantly help to control appetite and accomplish weight loss.

Among the intragastric balloons described in the prior art, one type remains connected to a filler tube during the entire period the balloon resides in the stomach. The balloon is introduced into the patient's stomach and a connected tube is extended through the nostril. Such an intragastric balloon is described, for example, in U.S. Pat. No. 4,133,315.

Another type of prior art intragastric balloon is placed into the stomach with the assistance of an appropriate plastic tube and usually a stylette. The balloon is filled with saline, whereafter the tube and stylette are withdrawn from the stomach. An intragastric balloon of this second type is described, for example, in UK Patent Application GB 2 090 747.

Even for the balloons of the second type, it may become desirable, from time-to-time, to add more fluid in order to further expand the balloon to optimize weight control. In addition, one means of removing the balloon is to deflate it by removing the saline from the balloon through a tube before the empty balloon is removed from the stomach.

To accomplish the foregoing, intragastric balloons of the second type are normally equipped with a self-sealing valve into which the filler tube and/or stylette can be inserted. One difficulty frequently encountered with this type of intragastric balloon is locating the valve when the balloon is already in the stomach and the surgeon attempts to reinsert the filler tube for the purpose of adding or removing fluid from the balloon.

Those skilled in the art will readily appreciate that manipulating the balloon while in situ to visually locate the valve is rather difficult, and the process of searching for the valve undesirably prolongs the procedure. Those experienced in the art will also readily appreciate that some intragastric balloons have been equipped with tabs for grasping the balloon for physical manipulation within the stomach and/or removal. For example, such tabs are shown in U.S. Pat. Nos. 5,084,061 and 6,746,460.

Even with the incorporation of such tabs into current intragastric balloon designs, the surgeon may still encounter significant difficulty in finding the valve for filling or removing fluid from the balloon. And even after the valve has been visually located, it is often still difficult or awkward for the surgeon to reinsert the filler tube into the example valve. The balloon may be slippery and positionally unstable. Additionally, spherical (or substantially spherical) intragastric balloons readily rotate in the stomach, so that even a slight disturbance of the balloon may place the filler valve into virtually any possible position relative to the filler tube poised to engage it.

Another problem associated with the heretofore known methods and devices is that following placement of the intragastric balloon, a patient may experience nausea from the interaction of the recently placed gastric balloon within the stomach. This has been particularly noted when the intragastric balloon is placed and filled to its capacity or substantially to its capacity in a single procedure.

Therefore, the present invention is directed at overcoming these problems associated with the prior art systems. These and other characteristics of the present invention will become apparent from the further disclosure to be made in the detailed description given below.

SUMMARY OF THE INVENTION

The present invention addresses the above-described problems by providing an apparatus and method for adjusting an inflatable intragastric balloon in situ. In contrast to the prior art devices described above, the inflatable intragastric balloon of the present invention has a grasping button or tab which allows the surgeon to capture and securely hold the intragastric balloon using a specialized gastroscopic instrument. The gastroscopic instrument also includes a filling instrument for adjusting the volume of fluid contained within the balloon.

More particularly, an intragastric balloon is provided with a combined grasping button/valve assembly. The surgeon deploys a gastroscopic instrument into a patient's stomach, for example, to capture and hold the intragastric balloon. The tip of the gastroscopic instrument is equipped with a grasping tool that securely fastens to the button portion of the button/valve assembly. Once the intragastric balloon is securely fastened to the instrument, a filling instrument is deployed through a self-sealing valve contained within the button/valve assembly. Once the filling instrument is deployed into the balloon, the surgeon may then add or remove a desired amount of fluid to adjust the size of the balloon to a desired volume. In this way, the surgeon is able to quickly adjust the volume of the balloon in a minimally invasive fashion, without requiring removal and re-implantation, or complete replacement of the balloon. In addition, the apparatus and method of the present invention significantly eliminates the difficulties in prior art devices of capturing and securely holding in situ an intragastric balloon.

According to another aspect of the invention, an intragastric balloon is provided that has a self-sealing surface portion and a grasping tab for securely fastening the gastroscopic instrument to the balloon. In this aspect, the self-sealing portion encompasses a portion or several portions of the surface of the balloon and allows for the surgeon to be less targeted in the deployment of a filling instrument, such as a needle. As described above, the surgeon deploys the gastroscopic instrument into the stomach and uses the grasping tool to capture one of the grasping tabs located on the surface of the balloon. The surgeon may then advance the filling instrument through one of the self-sealing surface portions of the balloon. Once fully advanced, the surgeon may adjust the volume of the balloon using the filling instrument. In this aspect, because the balloon has one or more self-sealing surfaces and/or grasping tabs, the surgeon has a number of locations to grasp the balloon and/or adjust its volume.

In addition to the aspects of the invention discussed above, the shape of the intragastric balloon of the present invention may be altered to that of a dual hemisphere, or other similar configuration. This allows for easier grasping of the intragastric balloon of the present invention.

In yet another aspect of the present invention, the intragastric balloon shell has a magnet embedded within the balloon shell or on the shell's surface. A corresponding magnetic surface is located on the tip of the gastroscopic instrument, which allows the surgeon to capture the balloon using magnetic force. This is yet another aspect of the present invention that significantly reduces the difficulties associated with the prior art.

In still another aspect of the present invention, an intragastric balloon has a recess that allows a surgeon to more easily position a needle or other instrument for filling and/or removing fluid from the balloon without the use of a grasping tool for capturing the balloon. The surgeon guides a needle or other filling-type instrument towards the conically-shaped recess, which has a valve or self-sealing portion located at the bottom of the recess. Several valve or self-sealing surface configurations may be implemented in this embodiment and located at the bottom of recess for filling or deflating of the balloon. These and various other aspects of the invention, and its advantages, will be discussed in more detail below.

Because of its in situ adjustability, the balloon can be filled over the duration of its placement, if desired, to improve weight loss over time. If weight loss is slow, the surgeon can add volume to the device to take up greater space in the stomach and encourage early satiety. With the improved weight loss over time, the device would benefit from a longer placement time while having a variable fill volume. To improve the duration of adjustability, the shell is preferably made from a highly acid resistant material such as diphenyl silicone, polytetrafluoroethylene (PTFE), modified PTFE, silicon-polyurethane elastomers, high density polyethylene (HDPE), low density polyethylene (LDPE) or other acid resistant shell materials. The shell may also be coated with a coating such as parylene to improve the acid resistance of device.

DETAILED DESCRIPTION OF THE PREFERRED EMBODIMENTS

The present invention is directed to a device and method for adjusting intragastric balloon volume in vivo or in situ, thereby avoiding the need to remove the balloon from the stomach.

Figure 1:
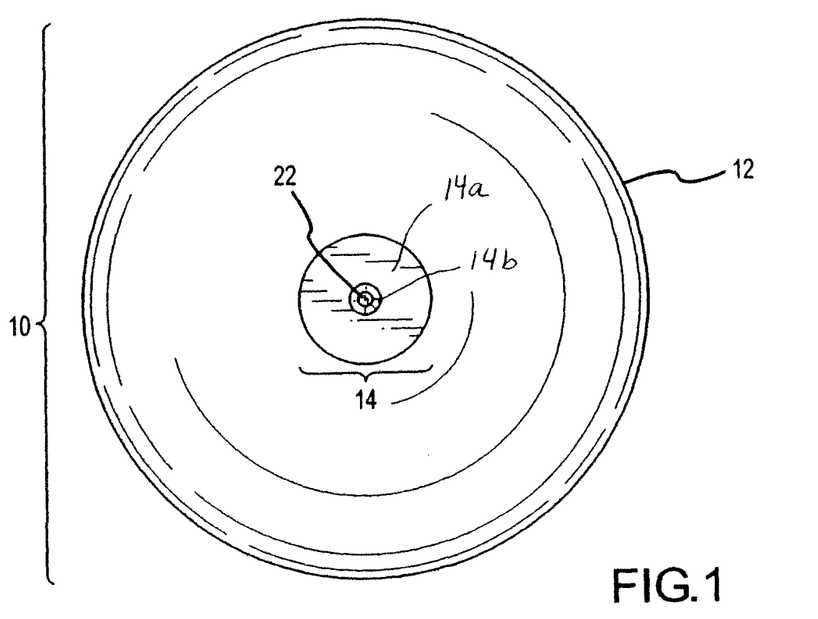
FIG. 1 is a top view of an intragastric balloon according to one embodiment of the present invention, which includes a combined grasping button/valve assembly.
Figure 2:
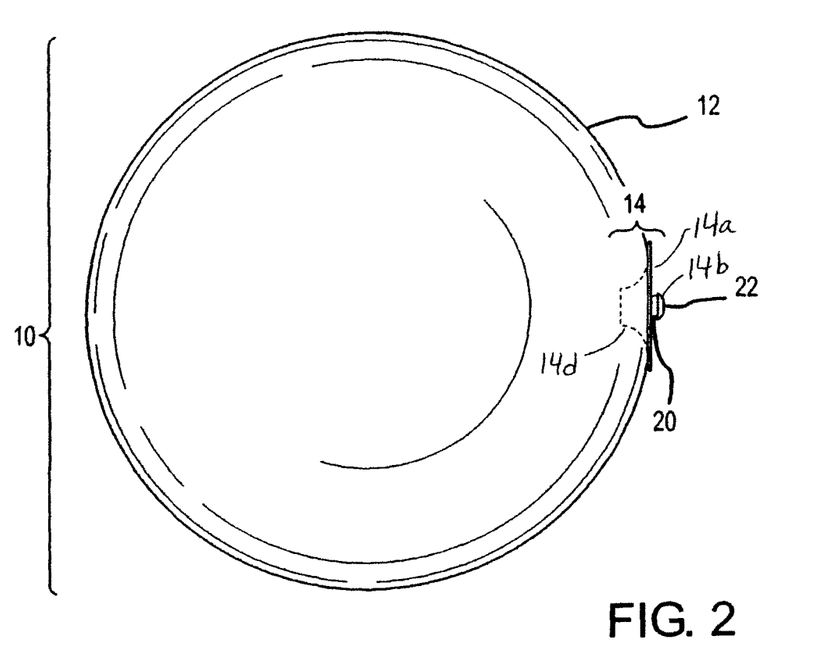
FIG. 2 is a side view of the intragastric balloon shown in FIG. 1.
Figure 3:
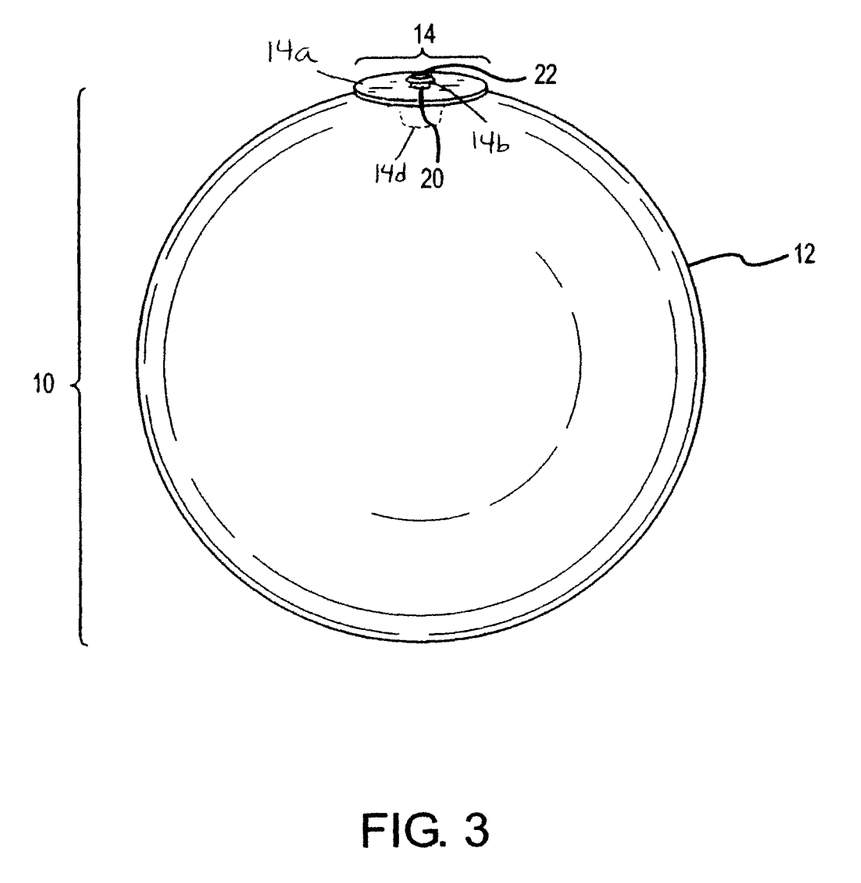
FIG. 3 is an elevated side view of the intragastric balloon shown in FIG. 1.

Referring to FIGS. 1-3, an intragastric balloon according to one preferred embodiment of the present invention is shown. The intragastric balloon 10 includes a shell 12 and a grasping button/valve assembly 14.

Figure 4:
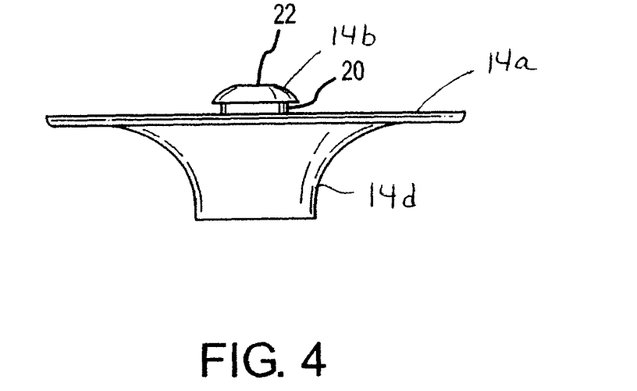
FIG. 4 is a side view of the grasping button/valve assembly of the intragastric balloon shown in FIG. 1.
Figure 5:
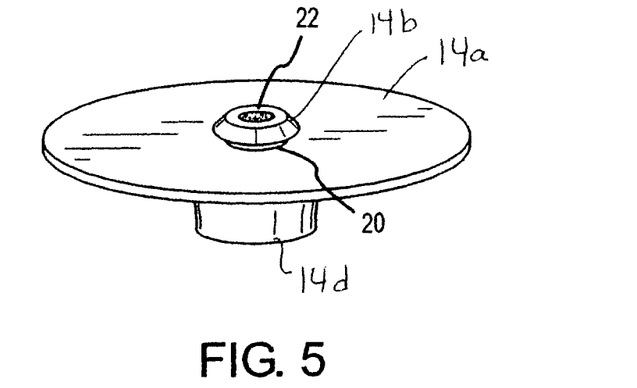
FIG. 5 is an elevated side view of the grasping button/valve assembly of the intragastric balloon shown in FIG. 1.
Figure 6:
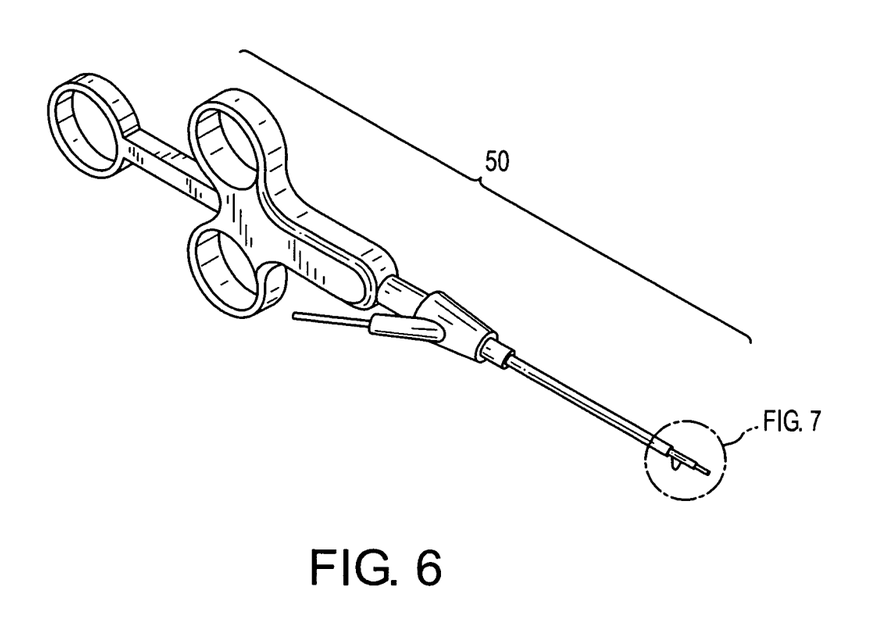
FIG. 6 is an elevated side view of a gastroscopic balloon adjustment instrument according to another embodiment of the present invention.

A method of adding or removing fluid, such as saline, from the intragastric balloon 10 according to the present invention requires that an intragastric balloon be implanted in a patient. During implantation, an uninflated balloon 10 may be positioned in the stomach in a desired location. A gastroscopic instrument, such as that shown in FIGS. 6-7 may be used to grasp the grasping button/valve assembly 14. FIGS. 4 & 5 show a close up view of the grasping button/valve assembly 14, which is integrated with the balloon shell 12. While the grasping tab of FIGS. 1-5 is a button configuration, those skilled in the art will appreciate that the tab may be in any number of configurations that may be substituted without departing from the scope of the invention. For instance, several loop configurations for the grasping tab are disclosed in FIGS. 8-10.

Figure 7:
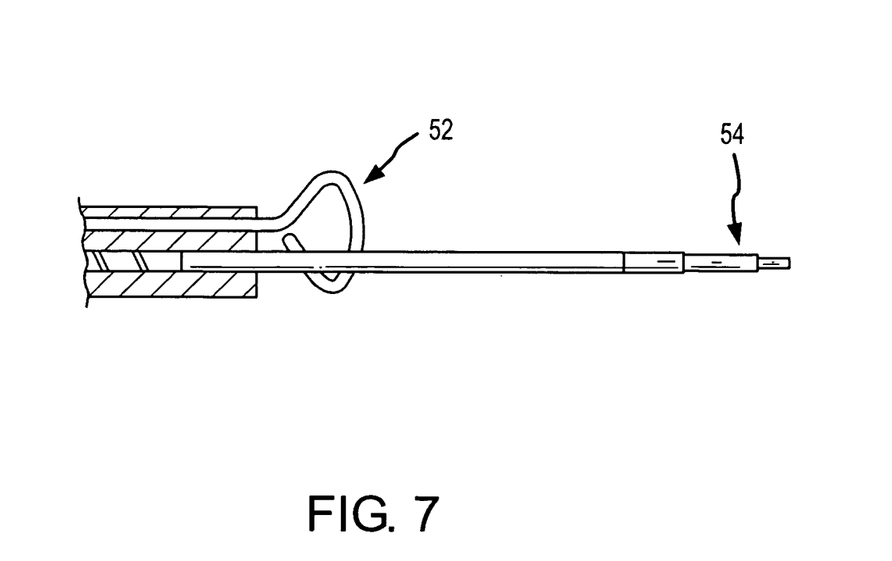
FIG. 7 is a close up view of the tip of the gastroscopic balloon adjustment instrument shown in FIG. 6.
Figure 15:
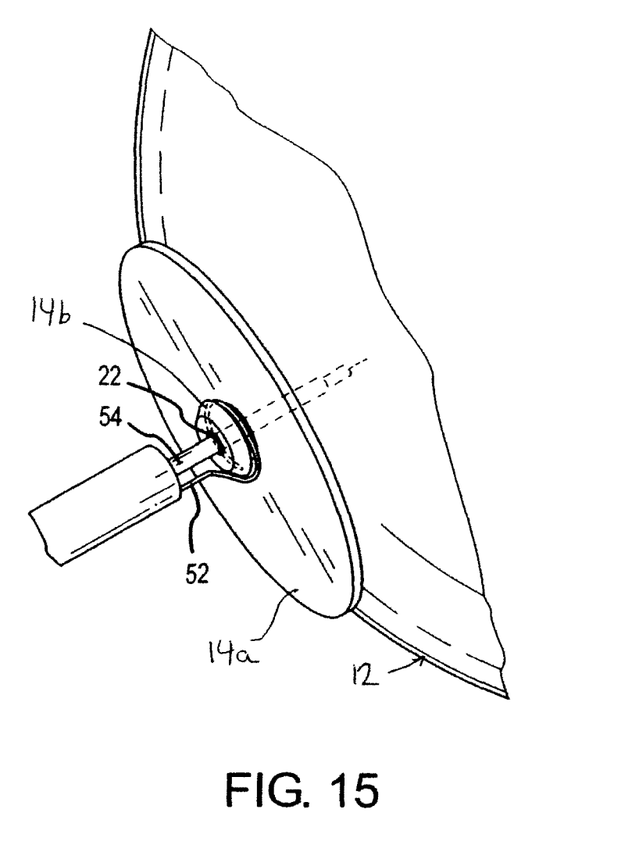
FIG. 15 is an elevated side of the grasping button/valve assembly of the intragastric balloon of FIGS. 1-3 being captured by the gastroscopic balloon adjustment instrument of FIGS. 6-7.

As can be seen in the close up view of FIG. 7, the instrument 50 includes a grasping tool 52 and needle 54. The surgeon performs the in situ adjustment as follows. The surgeon manipulates the gastroscopic instrument of FIGS. 6-7 to capture the button grasping button/valve assembly 14 shown in FIGS. 1-5. For example, as shown in FIGS. 1-4, the grasping button/valve assembly 14 includes a relatively wide proximal flange 14a interfacing an outer surface of the shell 12, and a relatively narrow distal flange 14b spaced apart from proximal flange 14a. The button ridge 20 is disposed between the proximal flange 14a and the distal flange 14b. Grasping button/valve assembly 14 further includes a depending portion 14d located in interior space of the shell cavity as shown. As shown most clearly in FIG. 5, the septum 22 is surrounded by distal flange 14b. Using the gastroscopic instrument, the surgeon positions grasping tool 52 in its "open" position to securely capture the grasping button/valve assembly 14 around the button ridge 20 such that the tool 52 is secured at button ridge 20 between proximal flange 14a and distal flange 14b, as shown in FIG. 15. The surgeon may then actuate the instrument 50 such that grasping tool 52 securely fastens to the balloon 10 by tightening the grasping tool around the button ridge 20. With the balloon securely fastened to the instrument, the surgeon may then advance the needle 54 of instrument 50 to pass through valve 22. FIG. 15 shows grasping tool 52 securely fastened around button ridge 20, with needle 54 advanced through valve 22. Valve 22 may be of a self-sealing septum type, comprised of a compressed silicone disc or other suitable material. Alternately, valve 22 may be a self-sealing leaf valve, slit valve, or the like. With the needle advanced through valve 22, the surgeon may then add the desired amount of fluid into the balloon. In the alternative, should the surgeon wish to remove a desired amount of fluid from the balloon, the surgeon may follow the same steps except use the needle to withdraw the desired amount of fluid.

Once a sufficient volume of fluid is added to or removed from the intragastric balloon, the surgeon retracts the needle back into the gastroscopic instrument. The grasping tool is then released from the grasping button. The gastroscopic instrument may then be removed from the patient, thus allowing for the procedure to be minimally invasive.

As an alternative to the self-sealing valve 22, the valve of the present invention may be of a "Two Way Slit Valve" type described in the commonly assigned international application published as WO 2005/007231, the disclosure of which is incorporated herein by reference. In addition, in the alternative to the needle 54 of the instrument described above, the gastroscopic instrument may have a filler tube with an injection tip of the type described in the above mentioned international application. In addition to the grasping button/valve assembly 14 described above for in situ adjustment of the balloon volume, balloon 10 may also include an additional quick-fill valve for use during the initial placement and filling of the balloon.

Figure 8:
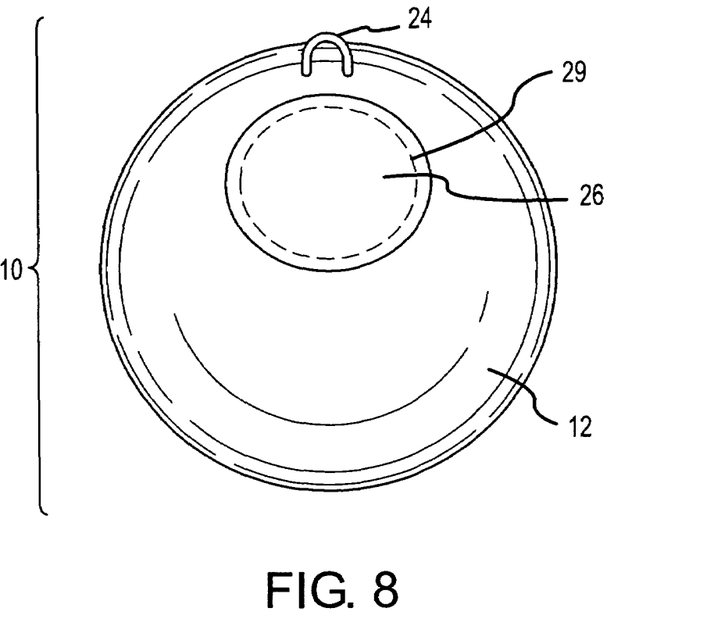
FIG. 8 is an elevated side view of an intragastric balloon according to another embodiment of the present invention, which includes a self-sealing shell portion and a loop tab for grasping.
Figure 9:
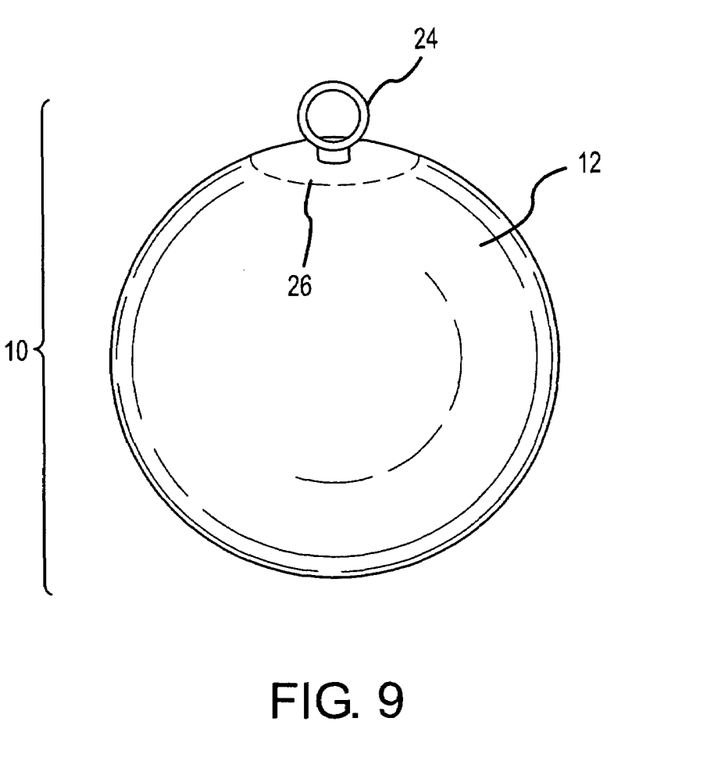
FIG. 9 is an elevated side view of an intragastric balloon according to yet another embodiment of the present invention, which includes a self-sealing shell portion with a loop tab incorporated on its surface.
Figure 10:
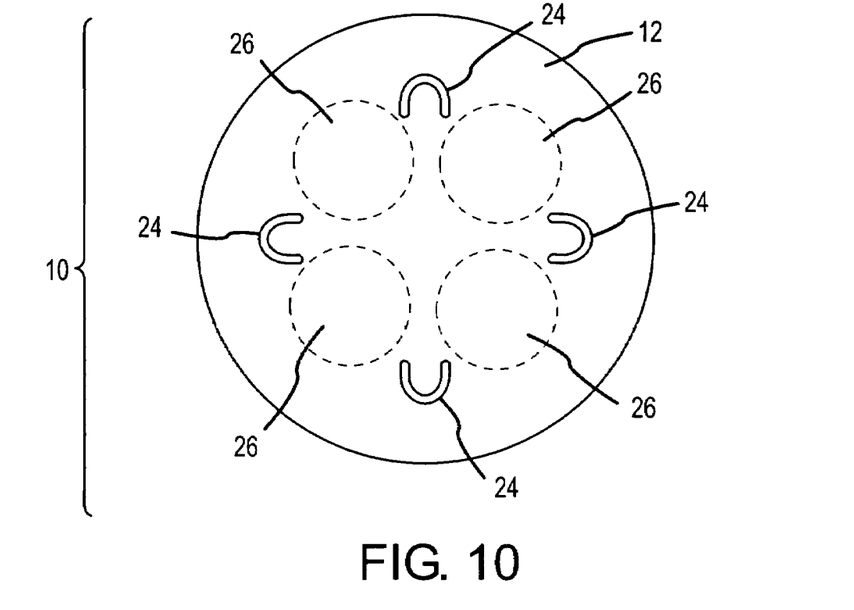
FIG. 10 is an elevated side view of an intragastric balloon according to yet another embodiment of the present invention, which includes several self-sealing shell portions and several grasping tabs.

FIGS. 8-10 show an intragastric balloon according to another embodiment of the present invention. Referring to FIG. 8, the intragastric balloon 10 includes a shell 12 and a grasping tab, such as a loop tab 24. The shell has a self-sealing shell portion 26 in place of the valve previously described. Similar to the first embodiment described above, using a gastroscopic instrument, the surgeon positions the grasping tool 52 in its "open" position to securely capture the grasping tab 24. The tip of the gastroscopic instrument 50 may be altered such that a hook or open ended loop may be used for grasping tool 52 in order to more easily capture loop tab 24. The surgeon may then actuate the instrument 50 such that grasping tool 52 securely fastens to the balloon 10 by tightening the grasping tool around grasping tab 24. A portion of the shell has a self-sealing surface 26. With the balloon securely fastened to the instrument, the surgeon may then advance the needle 54 of instrument 50 to pass through self-sealing surface 26. Balloon 10 may include visual markers 29, as shown in FIG. 8, to allow the surgeon to visually confirm the proper placement of the needle on the shell before piercing the self-sealing portion using the gastroscopic instrument. With the needle advanced through self-sealing surface 26, the surgeon may either fill or deflate the balloon as discussed above.

Self-sealing surface 26 may be comprised of a thicker tear resistant material, such as silicone or elastomer. Alternatively, the inner surface of self-sealing surface 26 could include gel or foam liners, such as silicones, hydrogels or elastomers, to seal in the area from the various needle punctures. Alternatively, any of these self-sealing means may be added to the entire shell 12 rather than just a portion 26 thereof to allow for easy puncturing with minimal need for manipulating the balloon to target a specific location.

FIGS. 9 & 10 illustrate further embodiments of the intragastric balloon of the present invention. FIG. 9 shows balloon 10, with shell 12, and self-sealing surface 26, whereby loop tab 24 is located centrally on self-sealing surface 26, thus allowing ease of locating, grasping, and insertion of needle 54. FIG. 10 shows balloon 10, shell 12, a plurality of self-sealing surfaces 26, and loop tabs 24. In this embodiment, multiple loop tabs and multiple self-sealing surfaces provide several options for the surgeon to properly position needle 54. In the embodiment of FIG. 10, the multiple self-sealing surfaces may each have a centrally located loop tab, as shown in the embodiment of FIG. 9.

In addition to the embodiments discussed above that include a self-sealing valve or surface, the entire shell may be comprised of a puncture-able, self-sealing shell. By adding hydrophilic materials to the inner lining of the balloon or adding the hydrophilic material into the shell in order to swell the shell, the full shell may be self-sealing. In addition, any of the methods discussed above for creating a self-sealing portion of the shell may be applied to the entire shell such that the entire shell becomes self-sealing. In this way, the balloon adjustment may be performed with just a gastroscopic needle, and a grasping tab is not needed to capture the balloon for adjustment. In this embodiment, the physician may puncture any portion of the balloon.

Figure 11:
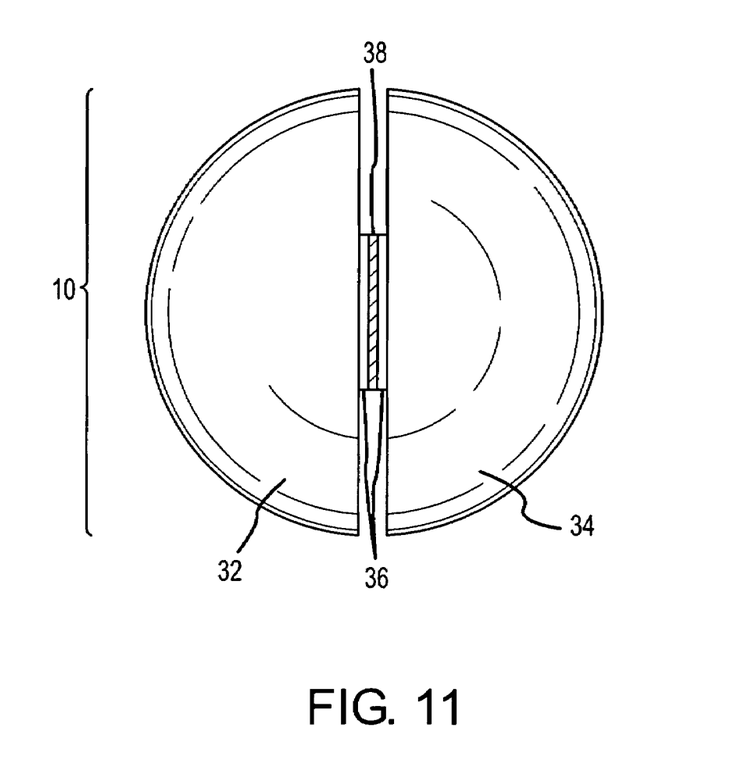
FIG. 11 is a side view of an intragastric balloon according to yet another embodiment of the present invention, which includes two balloon hemisphere portions and a connecting portion with a self-sealing surface.

FIG. 11 shows a further embodiment of the present invention. Intragastric balloon 10 includes a first hemisphere shell portion 32, a second hemisphere shell portion 34, and a connecting portion 36. Connecting portion 36 is self-sealing and connects the two hemisphere portions 32 and 34. In adjusting the gastroscopic balloon of FIG. 11, a gastroscopic instrument similar to that shown in FIGS. 6 & 7 may be used. Using the gastroscopic instrument, the surgeon would position the grasping tool 52 in its "open" position to securely capture the balloon 10. Grasping tool 52 may open to a large enough circumference to allow it to fit over one of the hemispheres in its entirety. Grasping tool 52 may then be positioned such that it is centered over connecting portion 36. The surgeon may then actuate the instrument 50 such that grasping tool 52 securely fastens to the balloon 10 by tightening the grasping tool around connecting portion 36. With the balloon securely fastened to the instrument, the surgeon may then advance the needle 54 of instrument 50 to pass through self-sealing surface 38. Self-sealing surface 38 may run the entire circumference of the connecting portion 36. In this way, properly securing the gastroscopic instrument 50 to the connecting portion ensures that the needle 54 will pass through the self-sealing surface 38. With the needle advanced through self-sealing surface 38, the surgeon may either fill or deflate the balloon as discussed above.

Figure 12:
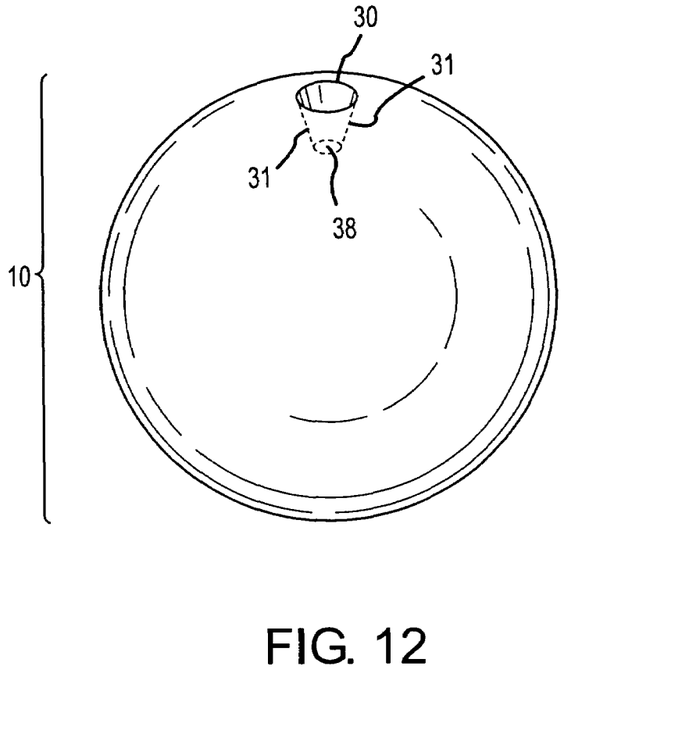
FIG. 12 is an elevated side view of an intragastric balloon according to yet another embodiment of the present invention, which includes a conical recess for receiving a gastroscopic instrument.

FIG. 12 shows a further embodiment of the present invention. Intragastric balloon 10 includes a frustaconical recess 30. Recess 30 allows the surgeon to more easily position a needle or other instrument for filling and/or removing fluid from the balloon without the use of a grasping tool for capturing the balloon. The surgeon guides a needle or other filling-type instrument towards the recess. Conical recess 30 has conically shaped walls 31 that guide the needle or other filling instrument to a valve or self-sealing portion located at the bottom of the recess as the instrument is advanced into recess 30. Any of the valve or self-sealing surface configurations discussed above may be implemented in this embodiment and located at the bottom of recess 30 for filling or deflating of the balloon.

Figure 13:
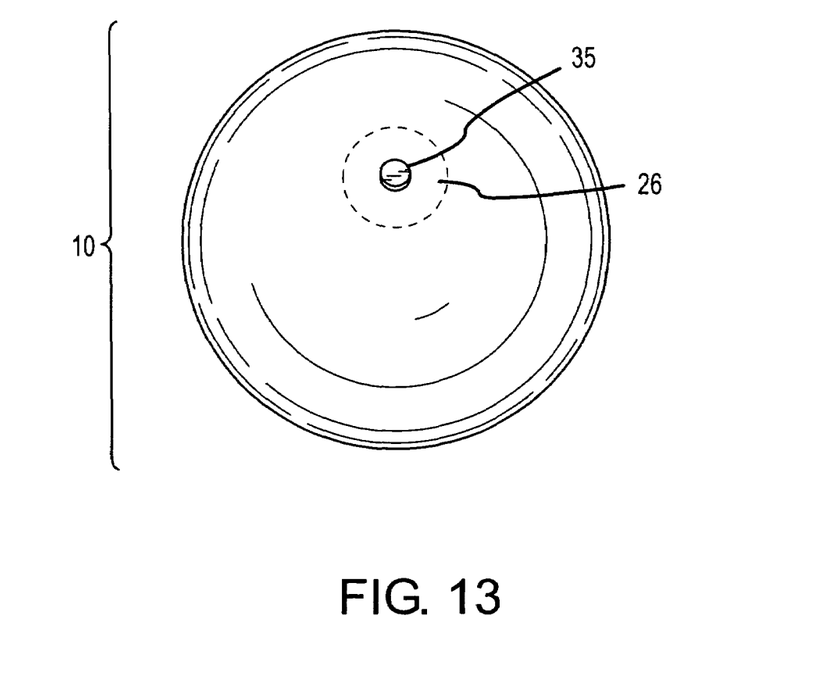
FIG. 13 is an elevated side view of an intragastric balloon according to yet another embodiment of the present invention, which includes a locating magnet on a self-sealing portion.
Figure 14:
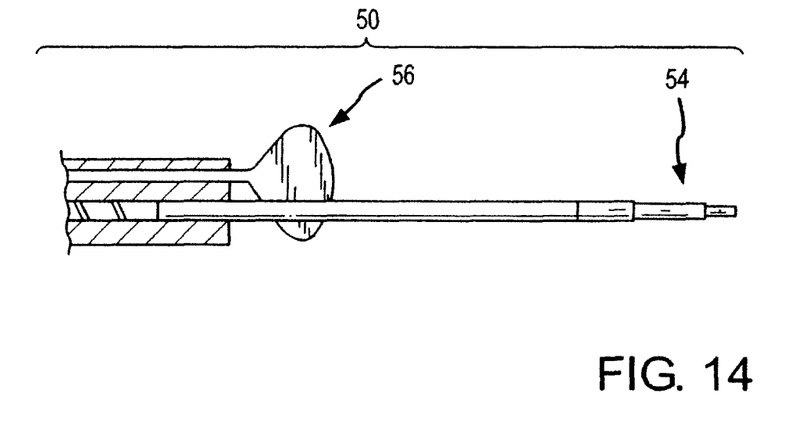
FIG. 14 is a close up view of a magnetic-tipped gastroscopic balloon adjustment instrument according to another embodiment of the present invention.

FIG. 13 shows still yet a further embodiment of the present invention. Intragastric balloon 10 has self-sealing portion 26 and magnet 35. FIG. 14 shows a close-up of the tip of a magnetic gastroscopic instrument used in conjunction with this balloon embodiment. Gastroscopic instrument 50 may be equipped with a magnet 56. As the surgeon advances the gastroscopic instrument 50 towards the balloon 10 in the stomach, magnet 35 of balloon 10 is attracted to magnet 56 of instrument 50, and in this way the surgeon is able to capture the balloon with the instrument. Once the balloon has been captured by the magnetic attraction between magnet 56 of instrument 50 and magnet 35 of balloon 10, the surgeon may advance needle 54 through self-sealing portion 26, and the surgeon may either fill or deflate the balloon as discussed above. The magnet may be placed in any number of desired locations, including on the inside or outside surface of the balloon or on the self-sealing portion itself. Alternatively, the magnet may be embedded in the balloon or self-sealing material.

EXAMPLES

The following examples, describing various procedures using the devices and methods of the present invention, are for illustrative purposes only and are not intended, nor should they be interpreted, to limit the scope of the invention.

Example 1

In Vivo Adjustment of a Balloon With a Button/Valve Assembly

In this example, the surgeon performs an in vivo adjustment of an intragastric balloon that has been previously implanted in a patient. In this example, the surgeon wishes to add more fluid to a previously implanted intragastric balloon that includes a grasping button/valve assembly, such as that shown in FIGS. 4 & 5. The gastroscopic instrument of this example is equipped with a camera, a needle for adding fluid, and a grasping tool for capturing the button of the button/valve assembly located on the surface of the intragastric balloon.

The patient is anesthetized, and the surgeon begins the procedure by inserting a gastroscopic instrument into the stomach. Using a camera located on a specially-configured gastroscopic instrument, such as that shown in FIGS. 6 & 7, the surgeon maneuvers the gastroscopic instrument into position to grasp the grasping button/valve assembly. The surgeon positions grasping tool 52 (FIG. 7) in its "open" position" around the button/valve assembly.

The surgeon then actuates the instrument 50 such that grasping tool 52 securely fastens to the balloon 10 by tightening the grasping tool around the button ridge 20. With the balloon securely fastened to the instrument, the surgeon advances the needle 54 of instrument 50 to pass through valve 22 (FIG. 15 shows the grasping tool securely fastened to the intragastric balloon).

With the needle advanced through valve 22, the surgeon adds the desired amount of fluid into the balloon.

Once a sufficient volume of fluid is added to the intragastric balloon, the surgeon retracts the needle back into the gastroscopic instrument. The grasping tool is then released from the grasping button. The gastroscopic instrument is then removed from the patient.

Example 2

In Vivo Adjustment of a Balloon With Self-Sealing Shell

In this example, the surgeon performs an in vivo adjustment of an intragastric balloon that has been previously implanted in a patient. In this example, the surgeon wishes to add more fluid to a previously implanted intragastric balloon that includes a self-sealing portion, such as that shown in FIG. 9, wherein a grasping tab is located on the self-sealing portion. The gastroscopic instrument of this example is equipped with a camera, a needle for adding fluid, and a grasping tool for capturing the grasping tab located on the surface of the intragastric balloon.

The patient is anesthetized, and the surgeon begins the procedure by inserting a gastroscopic instrument into the stomach. Using the camera located on a specially-configured gastroscopic instrument, such as that shown in FIGS. 6 & 7, the surgeon maneuvers the gastroscopic instrument into position to grasp the grasping tab 24. The surgeon positions the grasping tool of the gastroscopic instrument in its "open" position" to grasp grasping tab 24.

The surgeon then actuates the instrument 50 such that grasping tool securely fastens to the balloon 10 by tightening the grasping tool around the grasping tab. With the balloon securely fastened to the instrument, the surgeon advances the needle 54 of instrument 50 to pass through valve 22 (FIG. 15 shows the grasping tool securely fastened to the intragastric balloon).

With the needle advanced through valve 22, the surgeon adds the desired amount of fluid into the balloon.

Once a sufficient volume of fluid is added to the intragastric balloon, the surgeon retracts the needle back into the gastroscopic instrument. The grasping tool is then released from the grasping button. The gastroscopic instrument is then removed from the patient.

Example 3

In Vivo Adjustment of a Balloon With Dual-Hemisphere Configuration

In this example, the surgeon performs an in vivo adjustment of an intragastric balloon that has been previously implanted in a patient. In this example, the surgeon wishes to add more fluid to a previously implanted intragastric balloon that is of a dual-hemisphere configuration, such as that shown in FIG. 11. The gastroscopic instrument of this example is equipped with a camera, a needle for adding fluid, and a grasping tool for capturing the intragastric balloon.

The patient is anesthetized and the surgeon begins the procedure by inserting a gastroscopic instrument into the stomach. Using the camera located on a specially-configured gastroscopic instrument, such as that shown in FIGS. 6 & 7, the surgeon maneuvers the gastroscopic instrument into position to fit over one of the hemispheres of the balloon. The surgeon positions the grasping tool of the gastroscopic instrument in its "open" position". The physician then positions grasping tool 52 such that it is centered over connecting portion 36 (FIG. 11).

The surgeon then actuates the instrument 50 such that grasping tool 52 securely fastens to the balloon 10 by tightening the grasping tool around connecting portion 36. With the balloon securely fastened to the instrument, the surgeon advances the needle 54 of instrument 50 to pass through self-sealing surface 38 of the connecting portion, which in this example runs the entire circumference of the connecting portion.

With the needle advanced through self-sealing surface 38, the surgeon adds the desired amount of fluid into the balloon.

Once a sufficient volume of fluid is added to the intragastric balloon, the surgeon retracts the needle back into the gastroscopic instrument. The grasping tool is then opened and removed from the hemisphere of the balloon. The gastroscopic instrument is then removed from the patient.

Example 4

In Vivo Adjustment of a Balloon With a Recess

In this example, the surgeon performs an in vivo adjustment of an intragastric balloon that has been previously implanted in a patient. In this example, the surgeon wishes to add more fluid to a previously implanted intragastric balloon of the type shown in FIG. 12, which includes a recess for accepting the gastroscopic instrument. The bottom of the recess in this example has a self-sealing portion for accepting a needle for filling the balloon. The gastroscopic instrument of this example is equipped with a camera, a needle for adding fluid, and a slightly pointed tip for guiding the instrument into the recess.

The patient is anesthetized and the surgeon begins the procedure by inserting a gastroscopic instrument into the stomach. Using the camera located on a specially-configured gastroscopic instrument, such as that shown in FIGS. 6 & 7, the surgeon maneuvers the gastroscopic instrument into position to place the tip instrument into the recess.

With the gastroscopic instrument properly positioned in the recess, the surgeon advances the instrument so that it reaches the bottom of the recess on the surface of the intragastric balloon. Once the gastroscopic instrument reaches the bottom, reaches the bottom of the recess, the surgeon advances the needle 54 of instrument 50 to pass through self-sealing surface located at the bottom of the recess.

With the needle advanced through self-sealing surface, the surgeon adds the desired amount of fluid into the balloon.

Once a sufficient volume of fluid is added to the intragastric balloon, the surgeon retracts the needle back into the gastroscopic instrument. The gastroscopic instrument is then removed from the patient.

Example 5

In Vivo Adjustment of a Balloon With a Magnet

In this example, the surgeon performs an in vivo adjustment of an intragastric balloon that has been previously implanted in a patient. In this example, the surgeon wishes to add more fluid to a previously implanted intragastric balloon that is of the type shown in FIG. 13, which includes a magnet located in a self-sealing portion for use in conjunction with the gastroscopic instrument. The gastroscopic instrument of this example is equipped with a camera, a needle for adding fluid, and a magnetic tip for capturing the magnet embedded in the self-sealing portion of the balloon.

The patient is anesthetized and the surgeon begins the procedure by inserting a gastroscopic instrument into the stomach. Using the camera located on a specially-configured gastroscopic instrument, such as that shown in FIGS. 6 & 7, the surgeon maneuvers the gastroscopic instrument into position to place the tip instrument in contact with the portion of the self-sealing portion of the balloon that contains the embedded magnet.

With the gastroscopic instrument properly positioned above the magnet in the balloon, the surgeon advances the instrument so that it comes in contact with the magnet located in the balloon and captures the magnet. With the balloon captured by the gastroscopic instrument, the surgeon advances the needle 54 of instrument 50 to pass through self-sealing surface of the balloon.

With the needle advanced through self-sealing surface, the surgeon adds the desired amount of fluid into the balloon.

Once a sufficient volume of fluid is added to the intragastric balloon, the surgeon retracts the needle back into the gastroscopic instrument. The gastroscopic instrument is then removed from the patient.

Although the invention has been particularly shown and described with reference to certain preferred embodiments, it will be readily appreciated by those of ordinary skill in the art that various changes and modifications may be made in the invention and specific examples provided herein without departing from the spirit and scope of the invention.

I claim:

1. An inflatable intragastric balloon, comprising:
  an acid resistant shell having an outer surface and defining a fillable cavity for containing a volume of fluid; and
  a grasping tab/valve assembly coupled to the acid resistant shell, the grasping tab/valve assembly comprising:
    a valve for adjusting the volume of fluid of the inflatable intragastric balloon in situ; and
    a grasping tab in which the valve is received, the grasping tab including:
      a distal flange surrounding the valve and extending outward from the valve, and surrounding a hole for a needle to pass through in order to pass through the valve, the distal flange having a proximal surface having a first edge at a first diameter and a distal surface having a second edge at a second diameter less than the first diameter, and wherein the distal flange has a convex circumferential surface that extends between the first edge and the second edge;
      a graspable button ridge having a diameter that is less than the first diameter of the distal flange;
      a proximal flange positioned such that the graspable button ridge is positioned between the proximal flange and the distal flange, and extending outward from the graspable button ridge to form a diameter that is greater than the first and second diameters of the distal flange and greater than the diameter of the graspable button ridge, and being spaced apart from the distal flange and inseparably connected to the distal flange and having a proximal surface oppositely facing the outer surface of the acid resistant shell; and a depending portion extending, at a first end at the proximal surface of the proximal flange to a second end axially spaced from the first end, the depending portion having a larger diameter at the first end than at the second end, the depending portion extending into and connected to the acid resistant shell, wherein the depending portion is defined by a concave sidewall surface between its first and second ends, and wherein the concave sidewall surface is concave when the valve is received in the grasping tab and when the valve is closed.

2. The intragastric balloon of claim 1, wherein said valve is a septum.

3. The intragastric balloon of claim 1, wherein said valve is a slit valve.

4. The intragastric balloon of claim 1, wherein said shell comprises at least one of diphenyl silicone, PTFE, silicone-polyurethane elastomer, HDPE, LDPE or parylene.

5. The intragastric balloon of claim 1 wherein the valve comprises a self-sealing septum.

6. The intragastric balloon of claim 1 wherein the valve comprises a silicone disc.

7. The intragastric balloon of claim 1 wherein the valve comprises a compressed silicone disc.

8. The intragastric balloon of claim 1 wherein the depending portion is located in an interior space of the fillable cavity.

9. The inflatable intragastric balloon of claim 1, wherein the proximal flange has a distal surface opposite the proximal surface, the distal surface having a flat shape.

10. The inflatable intragastric balloon of claim 9, wherein the distal flange has a proximal surface with a flat shape that faces and extends parallel to the distal surface of the proximal flange.

11. The inflatable intragastric balloon of claim 10, wherein the graspable button ridge extends away from the proximal flange in a direction, the distal surface of the proximal flange and the proximal surface of the distal flange both extending in a direction that is perpendicular to the direction of the graspable button ridge.

12. The inflatable intragastric balloon of claim 1, wherein an outer edge of the distal flange has a circular shape that surrounds the valve.

13. The inflatable intragastric balloon of claim 1, wherein an outer edge of the proximal flange has a circular shape.

14. The inflatable intragastric balloon of claim 1, wherein the hole has a circular shape.

15. The inflatable intragastric balloon of claim 1, wherein the diameter of the proximal flange is larger than the diameter of the first end of the depending portion.

16. The inflatable intragastric balloon of claim 1, wherein the depending portion is defined by a depending surface between the first end at the proximal surface of the proximal flange and the second end, wherein a portion of the depending surface that extends at least from the first end is continuously tapered.

17. The inflatable intragastric balloon of claim 16, wherein the taper of the portion of the depending surface is concave and wherein the acid resistant shell contacts the concave surface.

18. An inflatable intragastric balloon, comprising:
an acid resistant shell having an outer surface and defining a fillable cavity for containing a volume of fluid;
a grasping tab/valve assembly coupled to the acid resistant shell, the grasping tab/valve assembly comprising:
a valve for enabling adjustment of the volume of fluid of the inflatable intragastric balloon in situ; and
a grasping tab in which the valve is received, the grasping tab including:
a distal flange surrounding the valve and extending outward from the valve, and surrounding a hole for a needle to pass through in order to pass through the valve, the distal flange having a proximal surface having a first diameter and a distal surface having a second diameter smaller than the first diameter;
a graspable button ridge having a diameter that is less than the first diameter of the distal flange;
a proximal flange positioned such that the graspable button ridge is positioned between the proximal flange and the distal flange, and extending outward from the graspable button ridge to form a diameter that is greater than the first and second diameters of the distal flange and greater than the diameter of the graspable button ridge, and being spaced apart from the distal flange and inseparably connected to the distal flange and having a proximal surface oppositely facing the outer surface of the acid resistant shell; and
a depending portion extending, at a first end at the proximal surface of the proximal flange to a second end axially spaced from the first end, the depending portion having a larger diameter at the first end than at the second end,
wherein the depending portion is defined by a depending sidewall surface between the first end at the proximal surface and the second end, and a portion of the depending surface extending from the first end is concave, and
wherein the acid resistant shell is attached to the concave portion of the depending surface, and
wherein the concave surface is concave when the valve is received in the grasping tab and when the valve is closed.

19. The inflatable intragastric balloon of claim 18 wherein the valve is a septum.

20. The inflatable intragastric balloon of claim 18 wherein the valve comprises a self-sealing septum.

21. The inflatable intragastric balloon of claim 18 wherein said valve is a slit valve.

22. The valve assembly of claim 18 wherein the valve comprises a silicone disc.

23. The valve assembly of claim 18 wherein the valve comprises a compressed silicone disc.

* * * * *